United States Patent [19]

Bunker

[11] Patent Number: 4,522,216
[45] Date of Patent: Jun. 11, 1985

[54] DENTAL FLOSS APPLICATOR

[76] Inventor: Robert L. Bunker, 429 Crowsmill Rd., Fords, N.J. 08863

[21] Appl. No.: 182,447

[22] Filed: Aug. 29, 1980

[51] Int. Cl.³ .............................................. A61C 15/00
[52] U.S. Cl. .................................................. 132/92 R
[58] Field of Search ...................................... 132/91, 92

[56] References Cited

U.S. PATENT DOCUMENTS

| | | | |
|---|---|---|---|
| 791,668 | 6/1905 | Apel et al. | 132/92 |
| 2,067,692 | 1/1937 | Cammack | 132/92 |
| 2,872,929 | 2/1959 | Rice | 132/91 R |
| 3,376,876 | 4/1968 | Wicklund | 132/92 R |
| 4,151,851 | 5/1979 | Bragg | 132/91 |

Primary Examiner—Robert Peshock
Attorney, Agent, or Firm—Thomas R. Farino, Jr.

[57] ABSTRACT

A dental floss applicator used for the removal of foreign substances lodged between the teeth as well as removal of plaque build up on all sides of a given tooth. The dental floss applicator comprises a solid rectangular shaped body fitted with a pair of adjacent end arms forming a yoke around which the floss is drawn so as to form an X-shaped pattern. A small button fastener on each side of the applicator body permit fastening of the floss after it has been stretched taut around the yoke.

4 Claims, 3 Drawing Figures

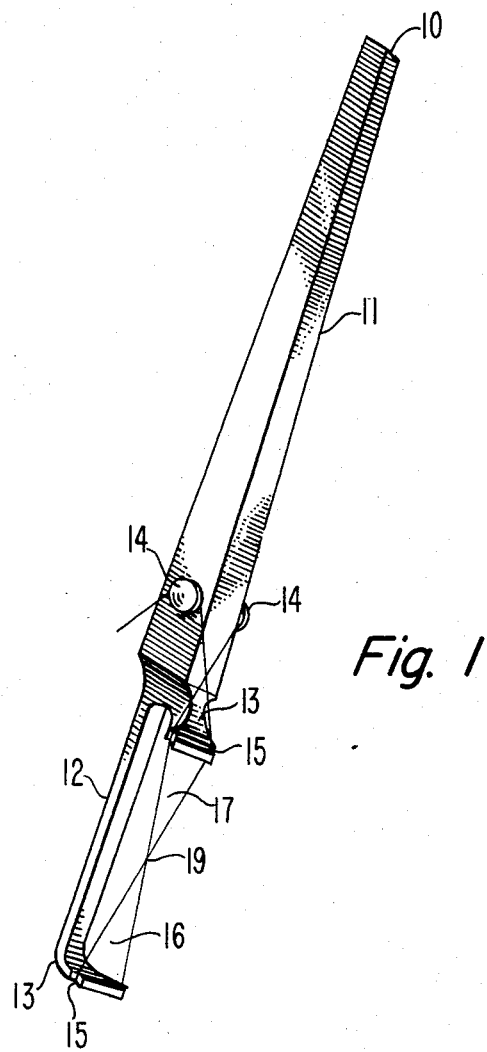
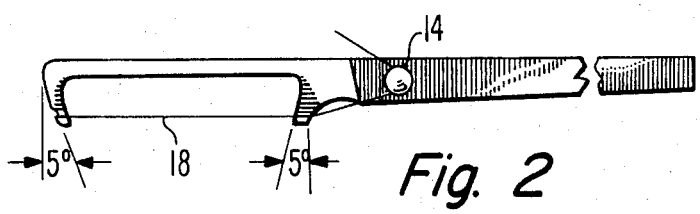
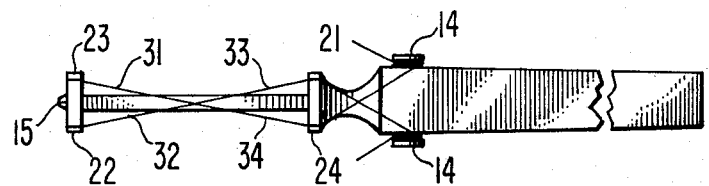

DENTAL FLOSS APPLICATOR

SUMMARY OF THE INVENTION

A dental floss applicator used for the removal of foreign substances lodged between the teeth and the removal of the gelatinous accumulation of bacteria and salivary mucin known as plaque from all sides of a given tooth.

It is acknowledged that dental floss holding tools are old in the art. Several designs are relatively complex, expensive to manufacture, and impractical to use for the marketing of dental floss in commerce. Holding tools having spaced apart prongs to hold a single strand of dental floss in taut condition for use in cleaning teeth are old and well known. These tools have been formed of many parts or have relied upon complex and expensive to manufacture screw tensioning means to gain tautness for the dental floss. In addition, many floss holders contain irregularly shaped projections which inadvertently have caused damage to teeth or lips or tongue during use of the tool.

The present invention provides the art with a much improved type of simplified implement for holding dental floss in a taut condition for the teeth cleaning operation. The article of the present invention is devoid of moving or screw threaded parts. It is simple to operate and maintain in a clean state. It is in the form of a solid rectangular shaped body fitted with a pair of adjacent end arms forming a yoke around which is drawn a single strand of dental floss so as to produce two criss crossed strands forming an X-shaped configuration for flossing. Two small button fasteners located one one each side of the applicator handle permit fastening of the two ends of the dental floss so as to achieve the necessary tautness for effective flossing.

The unique X-shaped configuration of floss permits the following advantages over conventional single strand flossing:

1. Flossing around the complete perimeter of the tooth is permitted.
2. A greater amount of working floss is in contact with each tooth.
3. Clean design for ease of cleaning and sterilizing.
4. Fast means for holding floss under tension. Surfaces are smooth and rounded at all corners and edges so as not to damage sensitive areas such as the lips and gums.

BRIEF DESCRIPTION OF THE DRAWING

The objects and features of the invention may be understood with reference to the following detailed description of an illustrative embodiment of the invention, taken together with the accompanying drawings in which:

FIG. 1 illutrates a perspective view of the invention;
FIG. 2 illustrates the side view of the invention;
FIG. 3 illustrates a top view of the invention.

DESCRIPTION OF THE PREFERRED EMBODIMENT

Turning now descriptively to the drawings in which similar reference characters denote similar elements throughout the several views, FIGS. 1 through 3 show the dental floss applicator 10 which is utilized for the removal of foreign subtances from between teeth as well as the removal of plaque build up from all sides of a given tooth.

The dental floss applicator 10 comprises a solid rectangularly shaped body 11 which serves as a handle during the dental flossing operation. The end of applicator 10 opposite handle 11 comprises an arm section 12 which terminates in two solid fingers 13 that are spaced apart to form a yoke.

Small button fastener 14 is mounted on each side of handle 11 for purposes of securing the dental floss and to maintain the desired tautness for proper flossing operation of the applicator. These low profile fasteners cause little interference in handling and use of the applicator. In addition, through the use of two fasteners it can readily be discerned which strand of floss is fastened to which button and further in which direction the floss is wound thereby permitting unwinding and disposal of used floss without confusion and tangle.

Fingers 13 contain a groove on the outside and side surfaces for purposes of seating and positioning the dental floss strand for purposes of forming the X-shaped configuration. Each finger 13 is angled 5 degrees towards each other from vertical as shown in FIG. 2 so as to provide maximum useage of the floss without interference to the teeth.

In use, a thread 18 of dental floss of approximately 10 inches in length is unwound from a commercially available spindle of floss, and is positioned on the arm section of applicator 10 by making approximately two wrappings of one end of the floss strand 18 around button 14, thus anchoring one end of the floss. The other end of the floss is then led into the side groove 24 of finger 13, into the side groove 23, back groove 15 and side groove 22, through the side groove 21 of finger 13 and then to button 14 where approximately two wrappings will secure the other end of floss strand 18 so as to produce a taut X-shaped configuration of floss comprised of two triangular portions 16, 17.

In the flossing operation, by placing a triangular section 16 or 17, of the X-shaped configuration over a given tooth, through lateral motion of the applicator handle 11, movement of the X-shaped configuration toward the intersection of the floss 19, will cause the intersection 19 to shift and conform to the contour of a given tooth, side strands 31, 32 making contact with the sides of the tooth and the intersection 19 making contact with the front or back of a given tooth depending upon the positioning of intersection point 19. If intersection point 19 is placed behind a given tooth the back or interior side of a given tooth will be cleaned. If the intersection point 19 is in front of a given tooth, the outside or front side of a tooth will be cleaned. Thus by placing a triangular section of the X-shaped configuration of floss over a tooth and moving the applicator towards the intersection point 19 of the floss, the intersection 19 will shift and conform to the contour of a given tooth providing, through linear motion of the applicator 10, simultaneous cleaning of three sides of a given tooth.

The X-shaped configuration embodied in this invention will readily adapt to any size tooth because of the continuous variation in width permitted between the floss strands.

The method of flossing embodied in the subject invention greatly simplifies flossing providing greater control with the elimination of having to work with ones fingers inside ones mouth.

The optimum size of the X-shaped configuration would be 0.400 inches and 1 5/8 inches in length; however, the invention described is not limited to this size.

Another advantage of the subject invention is the extraordinarily simple design of this floss applicator as compared to prior art teeth cleaning implements which permit economical means of mass production by techniques such as injection molding of organic plastic material.

Since obvious changes may be made in the specific embodiment of the invention described herein, such modifications being within the spirit and scope of the invention claimed, it is indicated that all matters contained herein is intended as illustrative and not as limiting in scope.

I claim:

1. A dental floss applicator for holding a section of dental floss exposed in taut engagement for dental use comprising:
    a handle section;
    an arm member integrally united to one end of the handle section, said arm member fitted at its free end with two spaced apart finger members forming a yoke, said fingers spaced at least 12.77 mm apart;
    a single strand of dental floss in an x-shaped configuration;
    means for holding and positioning (a) said single strand of floss in an x-shaped configuration the intersection of said x-shaped configuration being equi-distant from said spaced apart fingers; and
    means for securing said floss in taut condition between said fingers (.) said x-shaped configuration permitting simultaneous cleaning of three sides of a given tooth through shifting of the intersection of said x-shaped configuration while engaging said applicator in reciprocal motion about a given tooth.

2. The combination as recited in claim 1 in which the means for holding and positioning said strand of floss comprise an annular groove about the circumference of the finger members.

3. The combination as recited in claim 2 in which the means for securing said floss in taut condition comprise button fasteners.

4. The combination as recited in claim 3 in which said finger members are angled inwardly 5 degrees from vertical.

* * * * *